United States Patent
Cimino

Patent Number: 6,129,701
Date of Patent: Oct. 10, 2000

[54] VENTED ASPIRATOR AND METHOD

[75] Inventor: William W. Cimino, Louisville, Colo.

[73] Assignee: Sound Surgical Technologies, LLC, Lafayette, Colo.

[21] Appl. No.: 09/196,042

[22] Filed: Nov. 19, 1998

[51] Int. Cl.[7] ................................................. A61M 1/00
[52] U.S. Cl. ............................................. 604/35; 604/30
[58] Field of Search ........................ 604/27, 30, 32–35, 604/39, 404, 118, 119, 128, 129, 902

[56] References Cited

U.S. PATENT DOCUMENTS

| | | | |
|---|---|---|---|
| 4,548,197 | 10/1985 | Kinoshita | 128/4 |
| 4,596,533 | 6/1986 | Lee . | |
| 4,735,605 | 4/1988 | Schwartz . | |
| 4,886,491 | 12/1989 | Parisi et al. | 604/22 |
| 5,013,300 | 5/1991 | Williams . | |
| 5,112,302 | 5/1992 | Cucin . | |
| 5,163,433 | 11/1992 | Kagawa et al. | 128/660.01 |
| 5,181,907 | 1/1993 | Becker . | |
| 5,348,535 | 9/1994 | Cucin . | |
| 5,429,596 | 7/1995 | Arias et al. | 604/21 |
| 5,447,494 | 9/1995 | Dorsey, III | 604/43 |
| 5,569,178 | 10/1996 | Henley . | |
| 5,643,198 | 7/1997 | Cucin | 604/22 |
| 5,665,101 | 9/1997 | Becker . | |
| 5,766,194 | 6/1998 | Smith | 606/167 |

Primary Examiner—Sharon Kennedy
Attorney, Agent, or Firm—Dorsey & Whitney LLP

[57] ABSTRACT

An improved surgical instrument for the removal of fragmented tissues and fluids from a patient through a small incision is disclosed. The instrument utilizes a source of suction and a source of irrigating fluid which suspends and dilutes the fragmented tissues and also provides a pressure vent to improve the speed and thoroughness of the procedure. A multi-lumen cannula is used to deliver the irrigating fluid to the operative site, to vent the operative site, and to remove the fragmented tissue and fluids from the operative site.

7 Claims, 8 Drawing Sheets

VENTED ASPIRATOR AND METHOD

TECHNICAL FIELD

This invention relates generally to surgical instruments, and, more particularly, to a surgical device for use in aspirating fragmented tissue and fluids from a patient.

BACKGROUND OF THE INVENTION

Liposuction is a surgical procedure for altering the human form, specifically by removal of localized deposits of fat tissues that are unresponsive to diet or exercise. The procedure is also known as suction lipectomy, lipolysis, and more recently as body contour surgery or body sculpting surgery. It is most often performed by plastic surgeons, although dermatologists, gynecologists, and other surgical specialties also perform the procedure.

The procedure is typically accomplished by inserting a small cannula through an incision in the skin, applying a suction source to the end of the cannula that remains outside of the body, and forcing the working end of the cannula forward and backward in the layer of fatty tissue. The fatty tissue is torn, crushed, or avulsed, and is then aspirated through small openings along the sides of the cannula near the tip and then through a central lumen in the cannula to a tissue canister placed in-line with the cannula and the suction source. The procedure may involve multiple incisions and many passes of the cannula in each incision to achieve the desired cosmetic effect for the patient.

A liposuction cannula is typically a small metal tube with a blunt, closed end at the tip. The blunt, closed end at the tip is intended to minimize damage to tissues as the device is thrust forward. Small openings along the sides of the cannula near the tip create passages between the tissue and the central lumen of the cannula, which is in fluid communication with a suction source, so that tissue and fluids can be aspirated. The suction causes the adipose tissue to be pulled into the openings along the sides of the cannula, and the blunt dissection provided by the surgeon's manipulation of the cannula tears the tissue. The fragments and released fluids are then aspirated through the openings along the sides of the cannula and then through the central lumen of the cannula. Thus, these types of cannulae are designed to accomplish two surgical objectives with a single device. First, they crush, tear, or avulse the fatty tissues such that the tissue fragments and fluids can pass through the openings in the sides of the cannula. Second, the suction source and the central lumen of the cannulae are used to aspirate the tissue fragments and fluids from the operative site.

The liposuction procedure is referred to as a 'closed' procedure because the operative site about the tip of the cannula is not directly visualized during the procedure due to the small incision size and the length of the liposuction cannula, which results in the tip area being buried inside the tissue. When a cannula is placed into the fatty tissue through the small incision, a seal is created between the outer surface of the cannula about and along its length and the fatty tissue, preventing the flow of any ambient pressure fluid, such as air, to the operative site about the tip of the cannula. When suction is applied, there exists low pressure inside the cannula at the operative site, the blunt tip area and the side openings, that pulls the tissue into the side openings which is then torn with the motion of the cannula. Because the seal prevents the flow of any ambient pressure fluid to the operative site about the tip or the cannula, the pressure about the tip of the cannula quickly drops to the pressure of the suction source, which is significantly below the ambient pressure. The combination of the above-mentioned seal and the fact that the pressure at the operative site about the tip of the cannula has dropped to the pressure of the suction source greatly reduces, if not completely eliminates, the surgeon's ability to remove tissue fragments and fluids from the operative site because the pressure differential between the operative site at the tip of the cannula and the suction source has been eliminated. Thus, fragments and fluids move not at all or very slowly through the cannula and suction tubing, or clog the tubing. The tip of the cannula must be withdrawn from the patient to such an extent that the seal is broken and the tip and side openings are exposed to ambient air pressure to clear the cannula and suction line. This phenomenon appears to the surgeon as a 'clogged' instrument or tubing set.

The liposuction procedure can be traumatic to the patient. The mechanical disruption of the tissues may result in, among other things, bleeding, bruising, temporary numbness, or swelling. The procedure can also be physically demanding on the surgeon because of the forces required to repeatedly push the cannula through the tissue. Further, the final cosmetic result is a function of the skill of the surgeon, the patient, and the type of surgical instrumentation used in the surgery.

Many patents disclose improvements and solutions for liposuction cannulae. U.S. Pat. No. 4,596,553 to Lee discloses a suction cannula with a guide bar attached to the cannula that is used to control the depth of the cannula in the tissue relative to the skin. U.S. Pat. No. 4,735,605 to Schwartz discloses a suction cannula with an outer tube with a longitudinal slot, and an inner tube with a spiral slot which is movable relative to the outer tube. U.S. Pat. No. 5,112,302 to Cucin has a suction cannula with a reciprocating means so that the cannula can be caused to reciprocate relative to the handle. U.S. Pat. Nos. 5,348,535 and 5,643,198, also to Cucin, have a suction cannula with a hollow outer cannula and a hollow inner cannula connected to a reciprocating means. The hollow inner cannula reciprocates within the hollow outer cannula so that tissue pulled into openings in the hollow outer cannula is sheared between the two cannulae. U.S. Pat. No. 5,181,907 to Becker has a tubular member with a plurality of longitudinally extending members projecting radially outward beyond the surface of the tubular member. U.S. Pat. No. 5,665,101 also to Becker has a method of cutting tissue with a rotary powered surgical instrument with an inner and an outer tube, both with cutting windows on the sides of the tubes. U.S. Pat. No. 5,569,178 to Henley has a source of rotary power, an outer tubing, and an inner tubing with flanges. U.S. Pat. No. 5,013,300 to Williams has a single lumen cannula, a handle, a control means for varying the suction forces, and a means to swivel the handle relative to the cannula. This patent includes a means to vent the tubing set from the handpiece back to the suction source, but does nothing to solve the same problem for the cannula. Consequently, the seal and clog problems persist.

While some of the patented devices have claimed improvements and solutions to liposuction cannulae for the problems of tissue trauma, surgeon fatigue, and cosmetic results, none address or appreciate the above-mentioned seal and clog problems and all of the prior devices incorporate tissue fragmentation and tissue aspiration capability in but one cannula. All of these devices are subject to clogging.

There is a need to improve the design of the prior patents to further reduce trauma to the tissues of the patient, resulting in reduced healing times, less bruising, less bleeding, and reduced pain. Accordingly, it is the object of the instrument disclosed herein to produce an improved surgical instrument for the removal of fragmented tissues and fluids from a patient in a closed procedure with minimal damage to remaining tissues and to further increase the speed and thoroughness of the procedure by eliminating the above-mentioned seal and clog problems inherent in this closed procedure and therefore eliminating the clogging of previous designs.

SUMMARY OF THE INVENTION

It is a general object of the present invention to provide an improved surgical instrument for the removal of fragmented tissues and fluids from a patient through a small incision.

It is a further object of the present invention to provide a surgical instrument for the above-mentioned purpose that causes minimal trauma to all contacted tissues and thus provides decreased healing time, decreased patient pain, and reduced swelling, bleeding, and bruising.

It is a still further object of the present invention to provide a surgical instrument for the aspiration of fragmented tissues of a patient that does not clog.

It is yet a still further object of the present invention to provide a surgical instrument for the aspiration of fragmented tissues of a patient that provides simultaneous aspiration and irrigation.

The aforementioned objects of the present invention are accomplished by separating the tissue fragmentation aspect of the liposuction procedure from the aspiration aspect of the procedure and by providing a pressure vent capability using a multi-lumen cannula that prevents clogging.

The instrument disclosed is specifically designed for aspiration of fragmented tissues and fluids from a patient, and thus is not primarily intended to be used to fragment, tear, or avulse tissues. The fragmentation of the tissues is preferably accomplished with other instruments or devices primarily designed for tissue fragmentation, for example, either a direct application of appropriate ultrasonic energy or a transdermal application of appropriate ultrasonic energy. Further, the disclosed surgical instrument may provide simultaneous suction and irrigation in separate passages of a multi-lumen cannula. The irrigation fluid may suspend and dilute the fragmented tissues, making aspiration easier. An irrigation passage of the multi-lumen cannula provides a pressure vent that solves the above-mentioned seal problem and therefore eliminates the clogging problem. A suction passage and the irrigation passage are sized and shaped so that the resistance to flow is approximately equal in each passage, appropriately adjusted for changes in the viscosity between the irrigant and the aspirant. Still further, a vent passageway is provided on a handle to change the suction between the suction passage in the cannula and ambient air about the handle so that the surgeon can control the application of the suction about the tip of the cannula from the handle. A switch may be provided on the handle to initiate or inhibit the flow of irrigation fluid through the irrigation passage in the cannula.

In general the surgical aspirator and irrigator system is comprised of a source of suction, a source of irrigation fluid, and a handle to be held and manipulated by the surgeon. The source of suction may be the wall suction present in the operating room or it may be from a separate suction pump specifically designed for the lipoplasty procedure. The preferred method to deliver the irrigation fluid is to use a peristaltic pump and tubing set. The handle has a suction connector for fluid communication with the source of suction and an irrigation connector for fluid communication with the source of irrigation fluid. The preferred connector for both suction and irrigation is a tubing barb threaded into the handle. The handle has a suction channel in fluid communication with the suction connector, an irrigation channel in fluid communication with the irrigation connector, and a vent passageway in fluid communication between the ambient air and the suction channel.

A multi-lumen cannula having at least two passages along an axis thereof is supported on the distal end of the handle. The preferred outside diameter for the multi-lumen cannula is between three and six millimeters. The multi-lumen cannula has a first passage for suction that is in fluid communication with the suction channel and a second passage for irrigation that is in fluid communication with the irrigation channel. The multi-lumen cannula has a cross-section perpendicular to the axis, the cross-section located anywhere along the length of the multi-lumen cannula. The first passage has a surface area of a unit length measured from the cross-section and a cross-sectional area at the cross-section. The surface area of a unit length of the first passage can be calculated by multiplying the total perimeter of the first passage measured in centimeters by a unit length, which is one centimeter. The total perimeter may have one component such as the inside circumference of a circular tube or it may have two components if one passage contains the other passage, in which case the total perimeter, for example, is the sum of the inside circumference of an outer circular tube and the outside circumference of a second circular tube contained within outer circular tube. The first passage has a resistive ratio that is the surface area of a unit length of the first passage divided by the cross-sectional area of the first passage. The second passage has a surface area of a unit length measured from the cross-section and a cross-sectional area of the second passage at the cross-section. The surface area of a unit length of the second passage can be calculated as described above using the dimensions of the second passage. The second passage has a resistive ratio that is the surface area of the unit length of the second passage divided by the cross-sectional area of the second passage. The resistive ratio of the first passage is between 0.5 and 1.5 times the resistive ratio of the second passage. The preferred value is slightly less than 1.0 to account for the increase in viscosity of the aspirant relative to the irrigant. Thus, it is preferred that the resistive ratio of the first passage be between 0.7 and 0.9 times the resistive ratio of the second passage.

In a preferred embodiment of the surgical aspirator and irrigator system the multi-lumen cannula may include a hollow outer tube with an inner surface about and along its length and a hollow inner tube residing within the hollow outer tube with an outer surface about and along its length. The preferred material for both tubes is thin-walled stainless steel tubing. The hollow inner tube has a lumen, preferably circular, the lumen being the second passage for irrigation. An annular space is located between the outer surface of the hollow inner tube and the inner surface of the hollow outer tube, the annular space being the first passage for suction.

In another embodiment of the surgical aspirator and irrigator system the multi-lumen cannula may include a hollow outer tube with an inner surface about and along its length and a hollow inner tube residing within the hollow outer tube with an outer surface about and along its length. The preferred material for both tubes is thin-walled stainless steel tubing. The hollow inner tube has a lumen, preferably circular, the lumen being the first passage for suction. An annular space is located between the outer surface of the hollow inner tube and the inner surface of the hollow outer tube, the annular space being the second passage for irrigation.

The multi-lumen cannula may include a patient tip disposed away from the distal end of the handle with a blunt or bullet-nosed shape. The blunt or bullet-nosed shape of the tip is to smooth passage of the multi-lumen cannula through the tissues, thereby reducing trauma to the tissues and reducing the force required by the surgeon to push the multi-lumen cannula through the tissues. The preferred material for the patient tip is stainless steel. Polymers such as polycarbonate, polyurethane, or polyethylene may also be used. There may be one or more ports in or near the patient tip for providing fluid communication between the tissue and the first passage of the multi-lumen cannula. The one or more ports may be part of the patient tip or they may be part of the multi-lumen cannula near the patient tip. There may be one or more holes in or near the patient tip for providing fluid communication between the second passage of the multi-lumen cannula and the tissue. The one or more holes may be part of the patient tip or they may be part of the multi-lumen cannula near the patient tip.

The handle of the surgical aspirator and irrigator system may include a vent valve operatively coupled to the vent passageway for selectively establishing fluid communication between the ambient air and the suction channel that passes through the handle when the vent valve is open. The preferred method for creating the vent valve is to provide access to the ambient air orifice of the vent passageway so that the surgeon can open or occlude the orifice with his thumb or finger. A sliding or rotating mechanism that opens or occludes the vent passageway may also be used.

The handle may include an irrigation control switch with an electrical connection to an irrigation controller located at and operatively connected to the source of irrigation fluid. The irrigation control switch is used for initiating or inhibiting the flow of irrigation fluid by electrically signaling the irrigation controller through the electrical connection in circuit therewith. The preferred style of irrigation switch is a two-position push-button toggle switch.

The preferred irrigation fluid is a supply of sterile, biocompatible irrigation fluid such as sterile saline. The irrigation fluid may be a supply of filtered, pressurized, biocompatible gas such as carbon dioxide or air.

In a further embodiment the surgical aspirator and irrigator system may include a supply of sterile, biocompatible irrigation fluid, a supply of filtered, pressurized, biocompatible gas, and a gas connector located on the handle in fluid communication with the supply of filtered, pressurized, biocompatible gas. The handle has a gas channel in fluid communication with the gas connector and a two-input one-output connector. The two-input one-output connector is also commonly referred to as a 'Y fitting'. A first input on the two-input one-output connector is in fluid communication with the gas channel passing through the handle and a second input on the two-input one-output connector is in fluid communication with the irrigation channel passing through the handle. The preferred method of creating the gas channel is to use a piece of silicone tubing between the gas connector and the first input. An output on the two-input one-output connector is in fluid communication with the second passage in the multi-lumen cannula. A gas control valve may be located on the handle. The gas control valve selectively opens or closes so that the gas channel passing through the handle is in fluid communication with the first input on the two-input one-output connector when the gas control valve is open or so that the gas channel is sealed from fluid communication with the first input on the two-input one-output connector when the gas control valve is closed. The preferable method of creating the gas control valve is to use a spring and wedge to pinch and occlude the gas channel that has been formed with a piece of silicone tubing.

A method of using an aspirator and irrigator system that has a source of suction and a source of irrigation fluid is also claimed. The method has the steps of inserting a multi-lumen cannula into fragmented medium, applying suction to a first passage of the multi-lumen cannula, irrigating through a second passage of the multi-lumen cannula, using a handle on the multi-lumen cannula to manipulate the aspirator and irrigator within the medium to the desired areas of fragmented medium, sucking and/or irrigating to most effectively remove fragmented medium, removing the aspirator and irrigator system from the fragmented medium.

BRIEF DESCRIPTION OF THE DRAWINGS

The novel features of the invention are set forth in the appended claims. The invention will be best understood by reference to the following figures when read in conjunction with the detailed description of the invention.

FIG. 1a is an end view of the multi-lumen cannula of FIG. 1.

FIG. 2a is an end view of the multi-lumen cannula of FIG. 2.

FIG. 3a is an end view of the multi-lumen cannula of FIG. 3.

FIG. 4 is a partial schematic representation of a patient tip for the multi-lumen cannula shown in FIG. 1 and FIG. 1a.

FIG. 5 is a partial schematic representation of a patient tip for the multi-lumen cannula shown in FIG. 2 and FIG. 2a.

FIG. 6 is a partial schematic representation of a patient tip for the multi-lumen cannula shown in FIG. 3 and FIG. 3a.

DETAILED DESCRIPTION OF THE INVENTION

Figure 1:
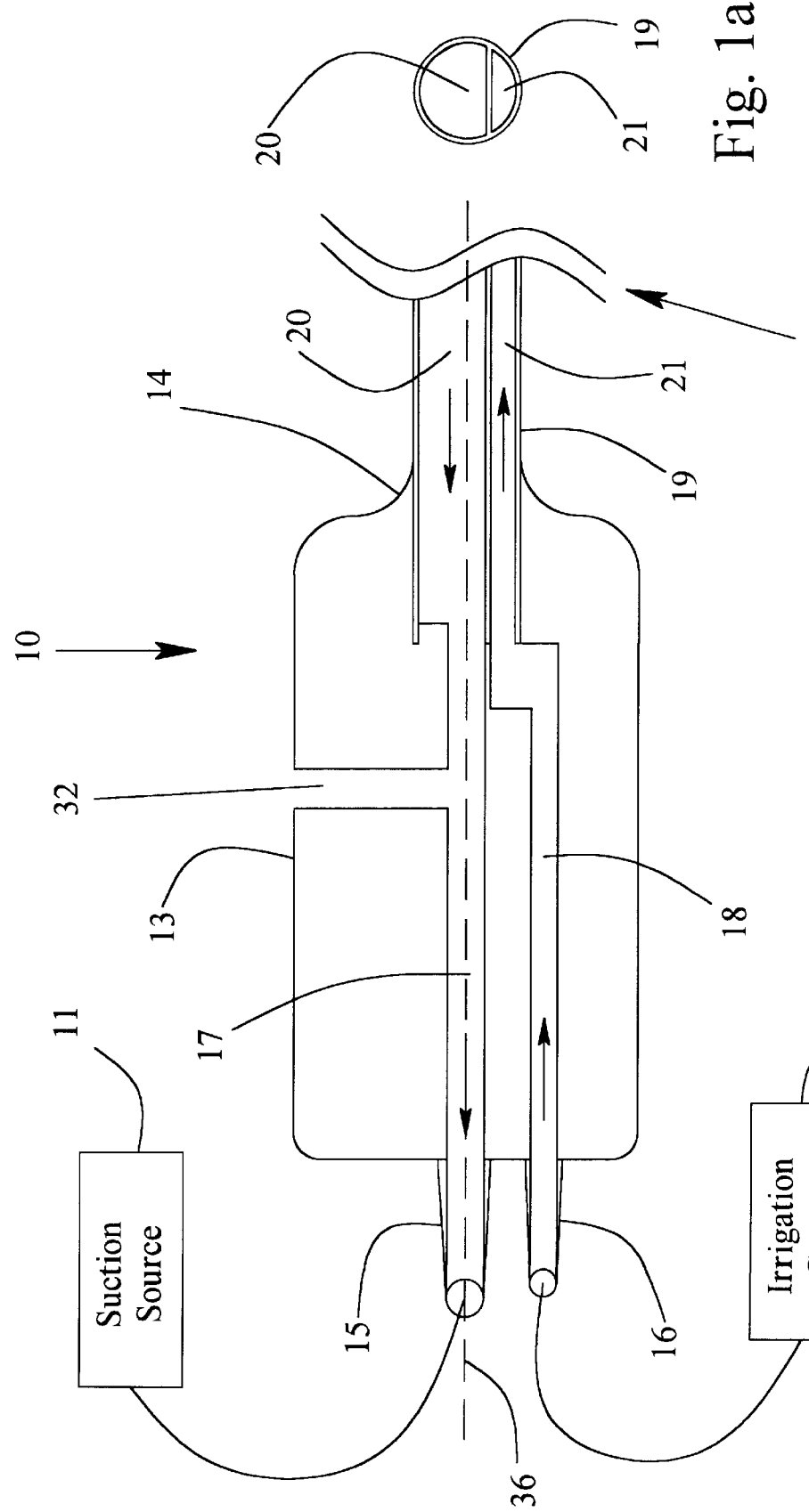
FIG. 1 is a partial schematic representation of the present invention.

Referring to the drawings, FIG. 1 is a partial schematic representation of the apparatus embodying this invention. In general the surgical aspirator and irrigator system 10 is comprised of a source of suction 11, a source of irrigation fluid 12, and a handle 13 to be held and manipulated by the surgeon. The source of suction may be the wall suction present in the operating room or it may be from a separate suction pump specifically designed for the lipoplasty procedure. The preferred method to deliver the irrigation fluid is to use a peristaltic pump and tubing set. The handle 13 has a suction connector 15 for fluid communication with the source of suction 11 and an irrigation connector 16 for fluid communication with the source of irrigation fluid 12. The preferred connector for both suction and irrigation is a tubing barb threaded into the handle 13. The handle 13 has a suction channel 17 in fluid communication with the suction connector 15, an irrigation channel 18 in fluid communication with the irrigation connector 16, and a vent passageway 32 in fluid communication between the ambient air about the handle 13 and the suction channel 17.

A multi-lumen cannula 19 having at least two passages along an axis 36 thereof is supported on the distal end 14 of the handle 13. The preferred outside diameter for the multi-lumen cannula is between three and six millimeters. The multi-lumen cannula has a first passage 20 for suction that is in fluid communication with the suction channel 17 and a second passage 21 for irrigation that is in fluid communication with the irrigation channel 18. The S-shaped double lines 37 shown in FIG. 1 indicate a break-in-length and are used to scale the diagram to fit on one page. The S-shaped double lines 37 are not part of the invention.

The multi-lumen cannula 19 has a cross-section perpendicular to the axis 36, the cross-section located anywhere along the length of the multi-lumen cannula, as shown in FIG. 1*a*. The first passage 20 has a surface area of a unit length measured from the cross-section and a cross-sectional area at the cross-section. The surface area of a unit length of the first passage 20 can be calculated by multiplying the total perimeter of the first passage 20 measured in centimeters by a unit length, which is one centimeter. The total perimeter may have one component such as the inside circumference of a circular tube or it may have two components if one passage contains the other passage, in which case the total perimeter, for example, is the sum of the inside circumference of an outer circular tube and the outside circumference of a second circular tube contained within outer circular tube. The first passage 20 has a resistive ratio that is the surface area of a unit length of the first passage 20 divided by the cross-sectional area of the first passage 20. The second passage 21 has a surface area of a unit length measured from the cross-section and a cross-sectional area of the second passage 21 at the cross-section. The surface area of a unit length of the second passage can be calculated as described above using the dimensions of the second passage 21. The second passage 21 has a resistive ratio that is the surface area of the unit length of the second passage divided by the cross-sectional area of the second passage 21. The resistive ratio of the first passage 20 is between 0.5 and 1.5 times the resistive ratio of the second passage 21. The preferred value is slightly less than 1.0 to account for the increase in viscosity of the aspirant relative to the irrigant. Thus, it is preferred that the resistive ratio of the first passage 20 be between 0.7 and 0.9 times the resistive ratio of the second passage 21.

Figure 2:
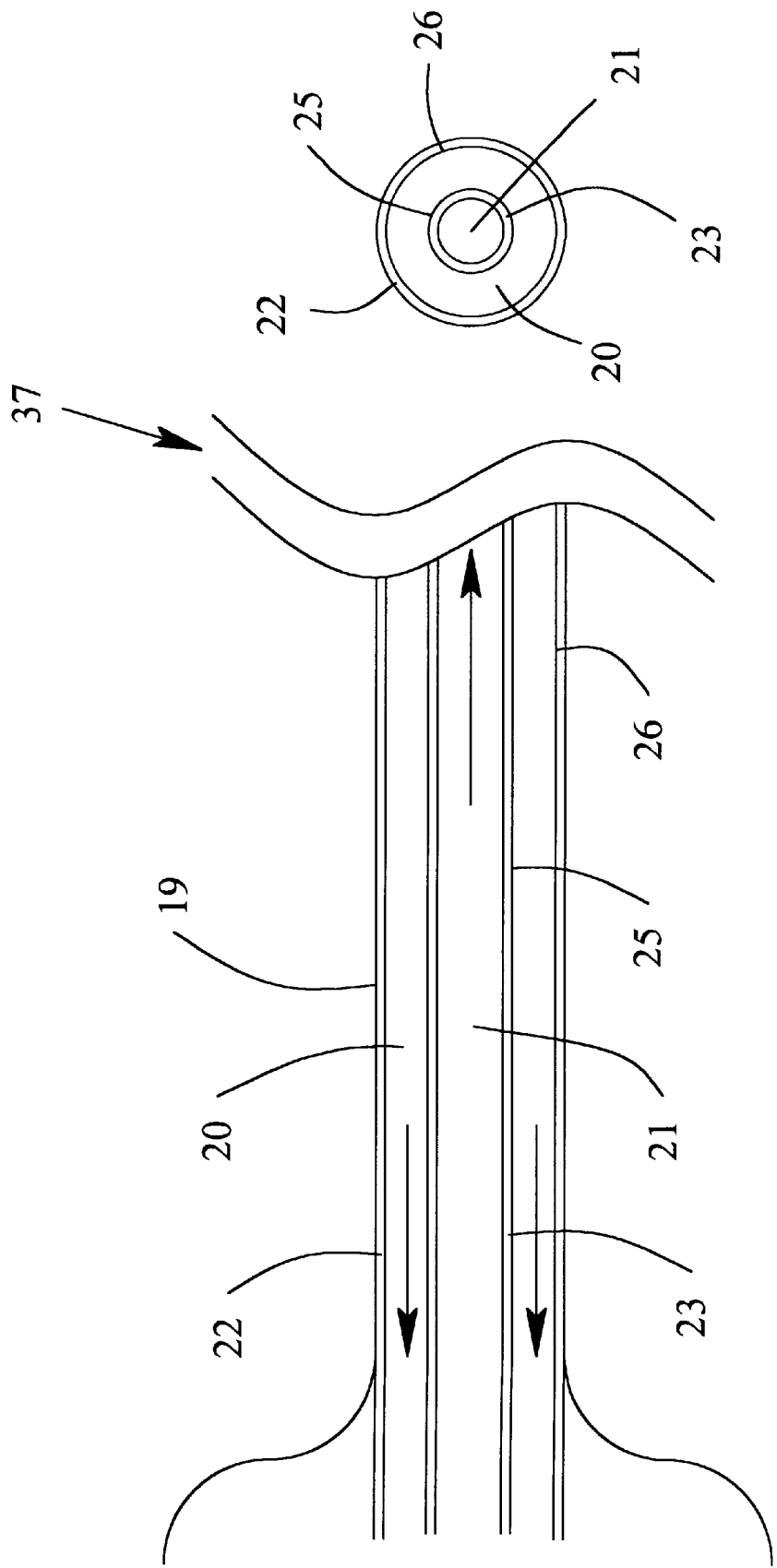
FIG. 2 is a partial schematic representation of the multi-lumen cannula with the irrigation passage being the lumen of the hollow inner tube.

The preferred embodiment of the multi-lumen cannula 19 is shown in FIG. 2. A cross-section of the multi-lumen cannula 19 for this embodiment is shown in FIG. 2*a*. The multi-lumen cannula 19 may include a hollow outer tube 22 with an inner surface 26 about and along its length and a hollow inner tube 23 residing within the hollow outer tube 22 with an outer surface 25 about and along its length. The preferred material for both tubes is thin-walled stainless steel tubing. The lumen of the hollow inner tube 23 is preferably circular and is the second passage 21 of the multi-lumen cannula 19 for irrigation. An annular space is located between the outer surface 25 of the hollow inner tube 23 and the inner surface 26 of the hollow outer tube 22, the annular space being the first passage 20 of the multi-lumen cannula 19 for suction. The S-shaped double lines 37 shown in FIG. 2 indicate a break-in-length and are used to scale the diagram to fit on one page. The S-shaped double lines 37 are not part of the invention.

Figure 3:
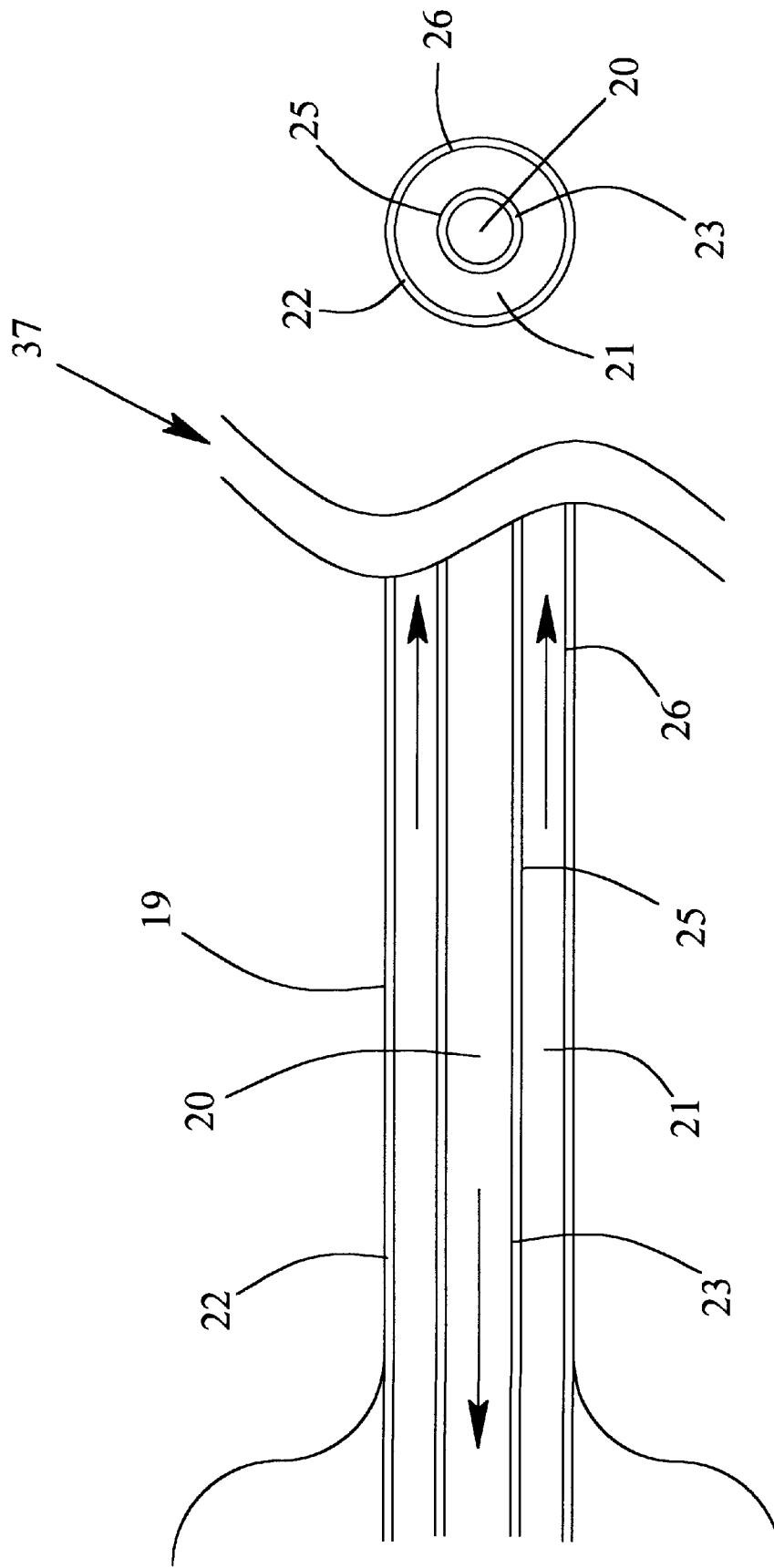
FIG. 3 is a partial schematic representation of the multi-lumen cannula with the suction passage being the lumen of the hollow inner tube.

Another embodiment of the multi-lumen cannula 19 is shown in FIG. 3. A cross-section of the multi-lumen cannula 19 for this embodiment is shown in FIG. 3*a*. The multi-lumen cannula 19 may include a hollow outer tube 22 with an inner surface 26 about and along its length and a hollow inner tube 23 residing within the hollow outer tube 22 with an outer surface 25 about and along its length. The preferred material for both tubes is thin-walled stainless steel tubing. The lumen of the hollow inner tube 23 is preferably circular and is the first passage 20 of the multi-lumen cannula 19 for suction. An annular space is located between the outer surface 25 of the hollow inner tube 23 and the inner surface 26 of the hollow outer tube 22, the annular space being the second passage 21 of the multi-lumen cannula 19 for irrigation. The S-shaped double lines 37 shown in FIG. 3 indicate a break-in-length and are used to scale the diagram to fit on one page. The S-shaped double lines 37 are not part of the invention.

Figure 4:
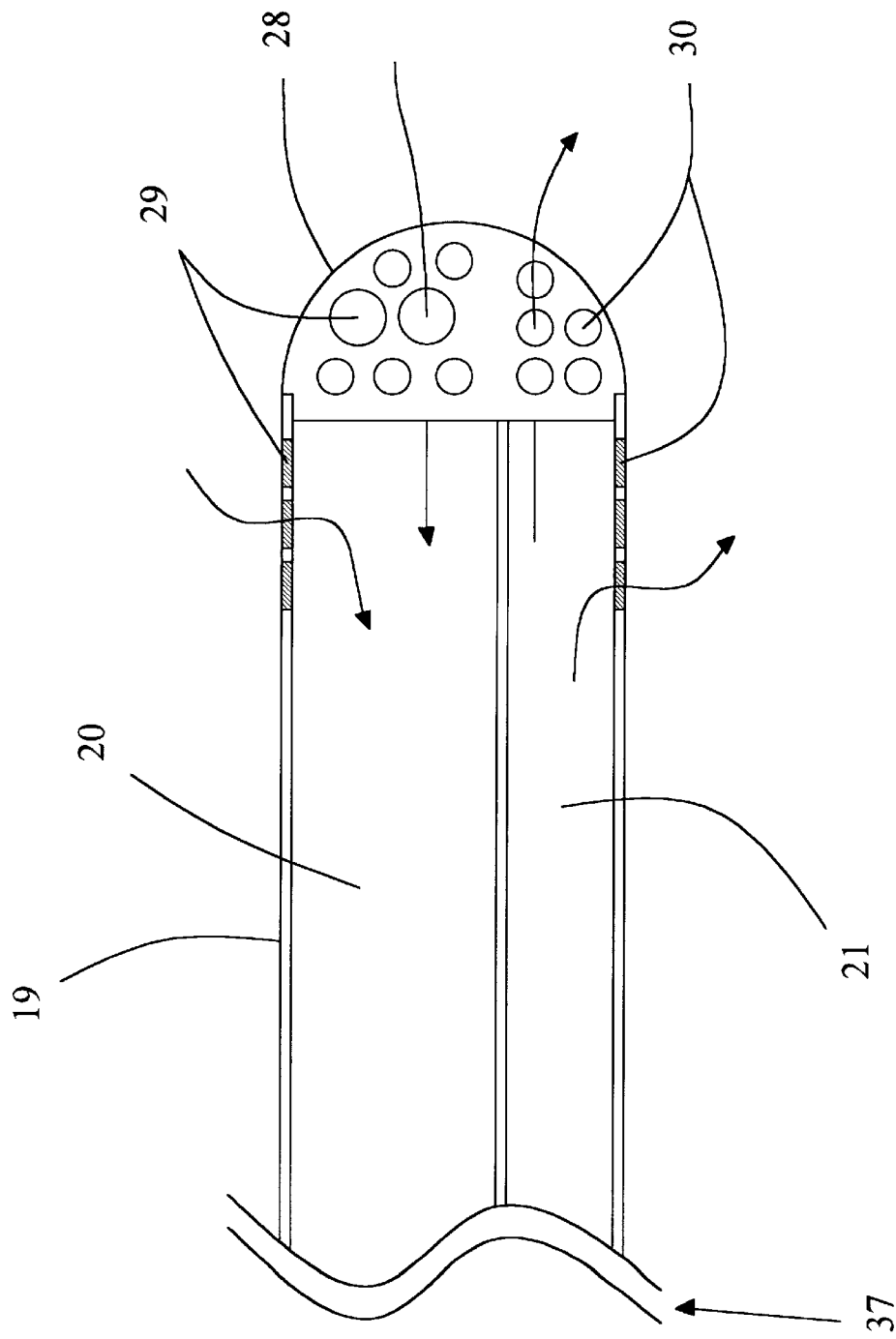

A partial schematic diagram of a patient tip 28 is shown in FIG. 4. The patient tip 28 shown in FIG. 4 mates with the multi-lumen cannula 19 shown in FIG. 1 and FIG. 1*a*. The patient tip 28 is disposed away from the distal end of the handle and has a blunt or bullet-nosed shape. The blunt or bullet-nosed shape of the tip is to smooth passage of the multi-lumen cannula 19 through the tissues, thereby reducing trauma to the tissues and reducing the force required by the surgeon to push the multi-lumen cannula 19 through the tissues. The preferred material for the patient tip is stainless steel. Polymers such as polycarbonate, polyurethane, or polyethylene may also be used. There may be one or more ports 29 in or near the patient tip 28 for providing fluid communication between the tissue and the first passage 20 of the multi-lumen cannula 19. The one or more ports 29 may be part of the patient tip 28 or they may be part of the multi-lumen cannula 19 near the patient tip 28. There may be one or more holes 30 in or near the patient tip 28 for providing fluid communication between the second passage 21 of the multi-lumen cannula 19 and the tissue. The one or more holes 30 may be part of the patient tip 28 or they may be part of the multi-lumen cannula 19 near the patient tip 28. The S-shaped double lines 37 shown in FIG. 4 indicate a break-in-length and are used to scale the diagram to fit on one page. The S-shaped double lines 37 are not part of the invention.

Figure 5:
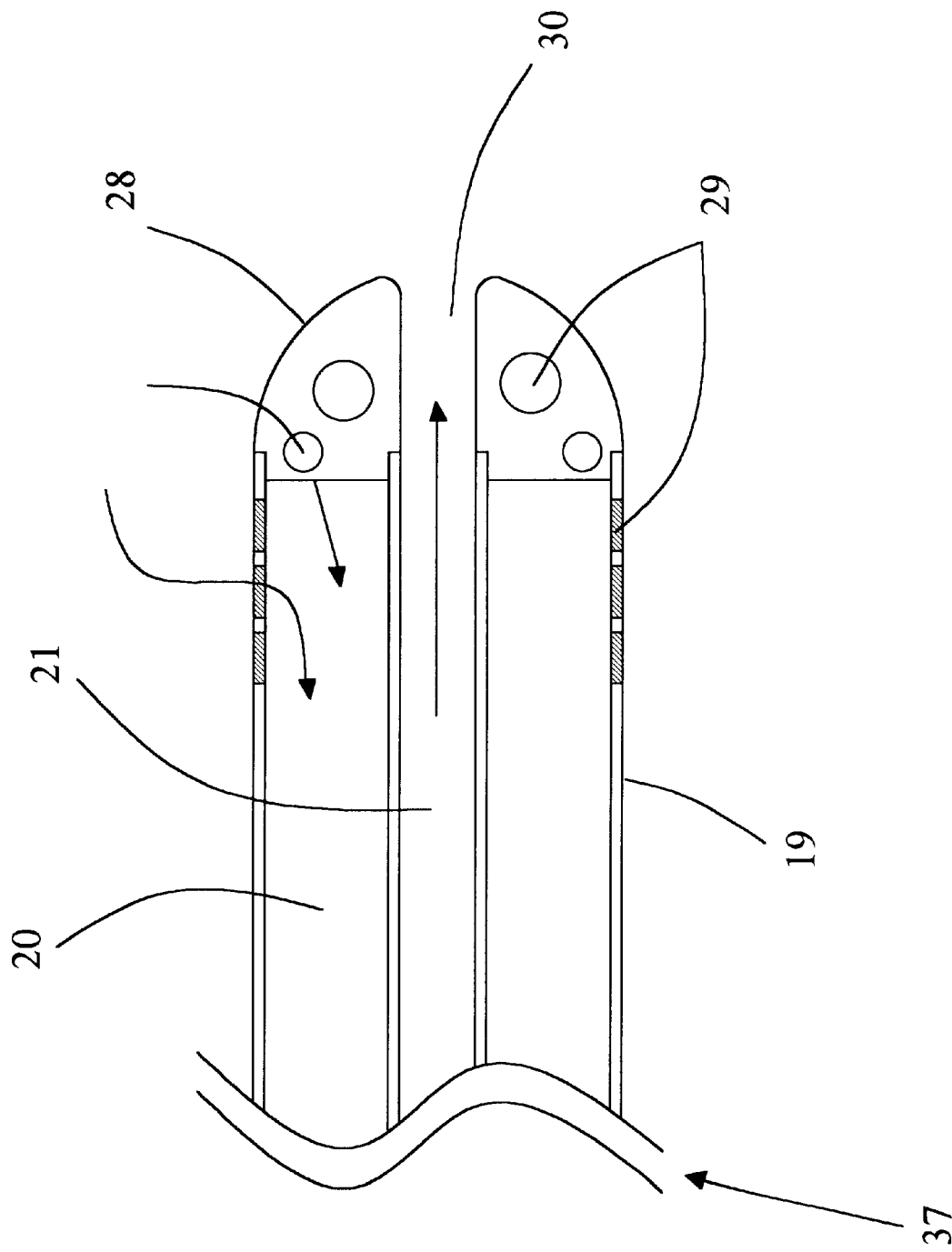

A partial schematic diagram of the preferred embodiment of a patient tip 28 is shown in FIG. 5. The patient tip 28 shown in FIG. 5 mates with the multi-lumen cannula 19 shown in FIG. 2 and FIG. 2*a*. The patient tip 28 is disposed away from the distal end of the handle and has a blunt or bullet-nosed shape. The blunt or bullet-nosed shape of the tip is to smooth passage of the multi-lumen cannula 19 through the tissues, thereby reducing trauma to the tissues and reducing the force required by the surgeon to push the multi-lumen cannula 19 through the tissues. The preferred material for the patient tip is stainless steel. Polymers such as polycarbonate, polyurethane, or polyethylene may also be used. There may be one or more ports 29 in or near the patient tip 28 for providing fluid communication between the tissue and the first passage 20 of the multi-lumen cannula 19. The one or more ports 29 may be part of the patient tip 28 or they may be part of the multi-lumen cannula 19 near the patient tip 28. There may be one or more holes 30 in or near the patient tip 28 for providing fluid communication between the second passage 21 of the multi-lumen cannula 19 and the tissue. The one or more holes 30 may be part of the patient tip 28 or they may be part of the multi-lumen cannula 19 near the patient tip 28. The S-shaped double lines 37 shown in FIG. 5 indicate a break-in-length and are used to scale the diagram to fit on one page. The S-shaped double lines 37 are not part of the invention.

Figure 6:
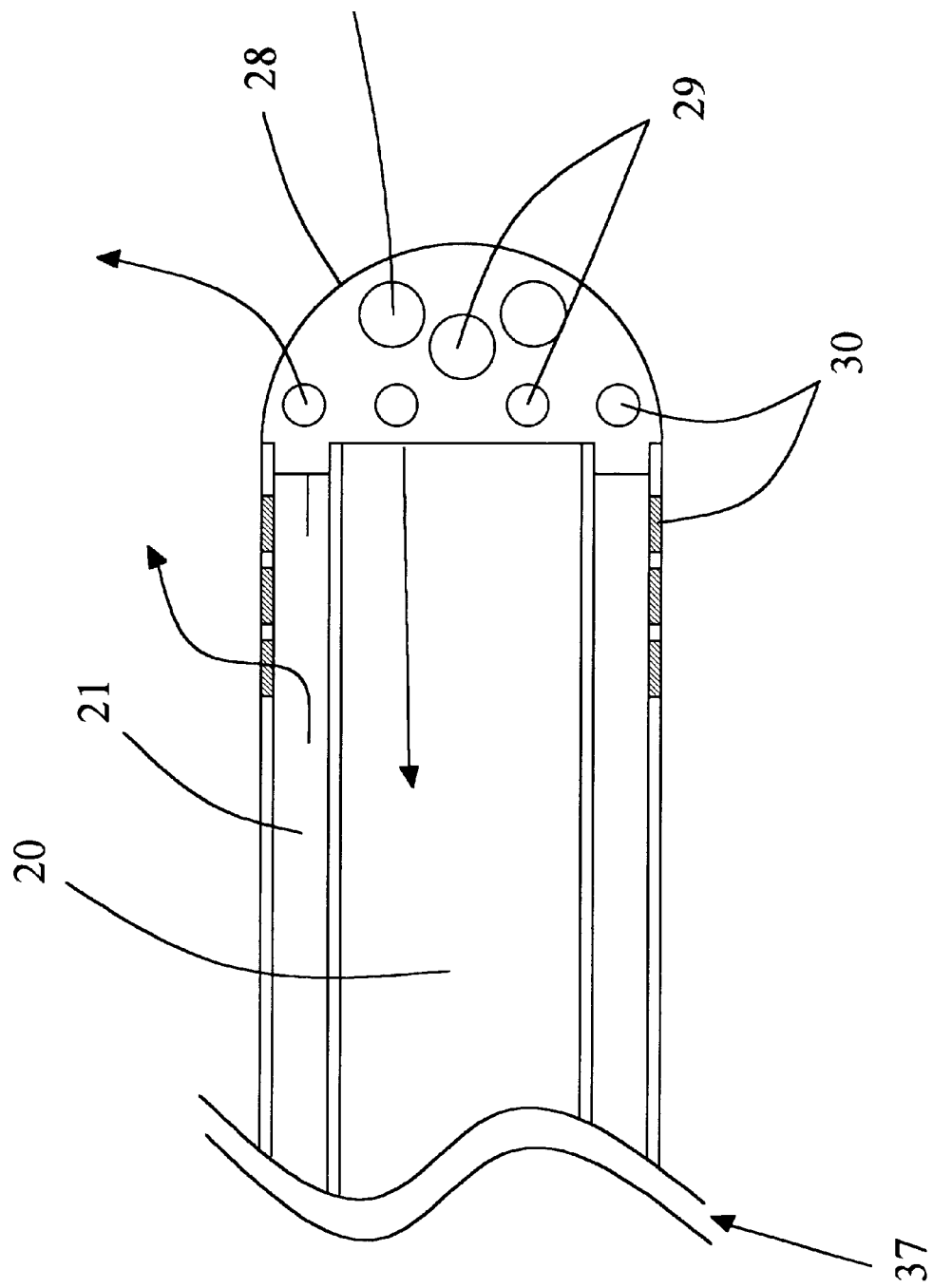

A partial schematic diagram of a third embodiment of a patient tip 28 is shown in FIG. 6. The patient tip 28 shown in FIG. 6 mates with the multi-lumen cannula 19 shown in FIG. 3 and FIG. 3a. The patient tip 28 is disposed away from the distal end of the handle and has a blunt or bullet-nosed shape. The blunt or bullet-nosed shape of the tip is to smooth passage of the multi-lumen cannula 19 through the tissues, thereby reducing trauma to the tissues and reducing the force required by the surgeon to push the multi-lumen cannula 19 through the tissues. The preferred material for the patient tip is stainless steel. Polymers such as polycarbonate, polyurethane, or polyethylene may also be used. There may be one or more ports 29 in or near the patient tip 28 for providing fluid communication between the tissue and the first passage 20 of the multi-lumen cannula 19. The one or more ports 29 may be part of the patient tip 28 or they may be part of the multi-lumen cannula 19 near the patient tip 28. There may be one or more holes 30 in or near the patient tip 28 for providing fluid communication between the second passage 21 of the multi-lumen cannula 19 and the tissue. The one or more holes 30 may be part of the patient tip 28 or they may be part of the multi-lumen cannula 19 near the patient tip 28. The S-shaped double lines 37 shown in FIG. 6 indicate a break-in-length and are used to scale the diagram to fit on one page. The S-shaped double lines 37 are not part of the invention.

Figure 7:
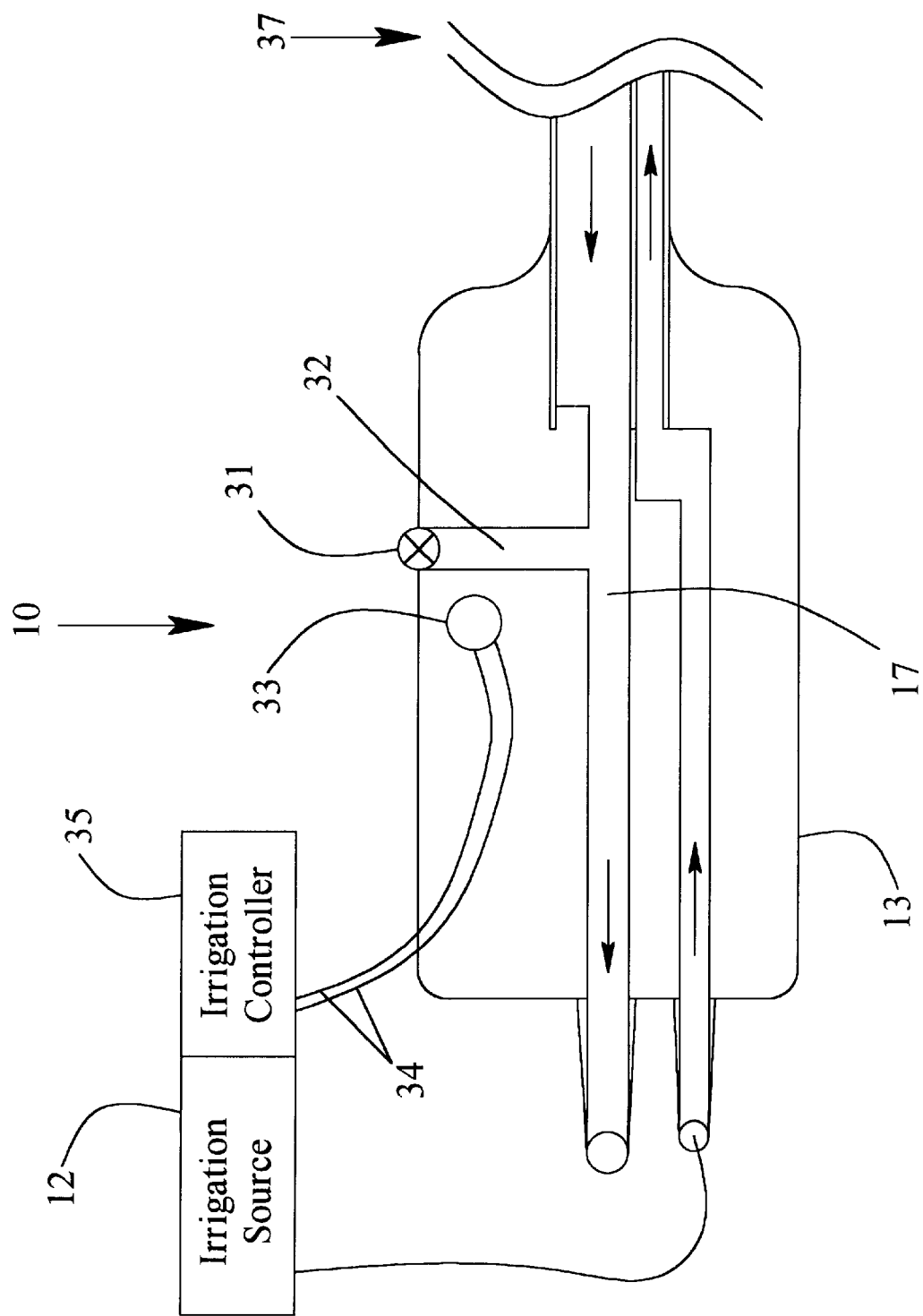
FIG. 7 is a partial schematic representation of the handle showing the vent valve, the vent passageway, the irrigation control switch, and the irrigation controller.

A partial schematic diagram of the handle 13 of the surgical aspirator and irrigator system 10 is shown in FIG. 7. The handle 13 may include a vent valve 31 operatively coupled to the vent passageway 32 for selectively establishing fluid communication between the ambient air about the handle 13 and the suction channel 17 that passes through the handle 13. The preferred method for creating the vent valve 31 is to provide access to the ambient air orifice of the vent passageway 32 so that a surgeon can open or occlude the orifice with his thumb or finger. A sliding or rotating mechanism that opens or occludes the vent passageway 32 may also be used.

The handle may include an irrigation control switch 33 with an electrical connection 34 to an irrigation controller 35 located at and operatively connected to the source of irrigation fluid 12. The irrigation control switch 33 is used for initiating or inhibiting the flow of irrigation fluid by electrically signaling the irrigation controller 35 through the electrical connection 34 in circuit therewith. The preferred style of irrigation switch is a two-position push-button toggle switch. The S-shaped double lines 37 shown in FIG. 7 indicate a break-in-length and are used to scale the diagram to fit on one page. The S-shaped double lines 37 are not part of the invention.

Figure 8:
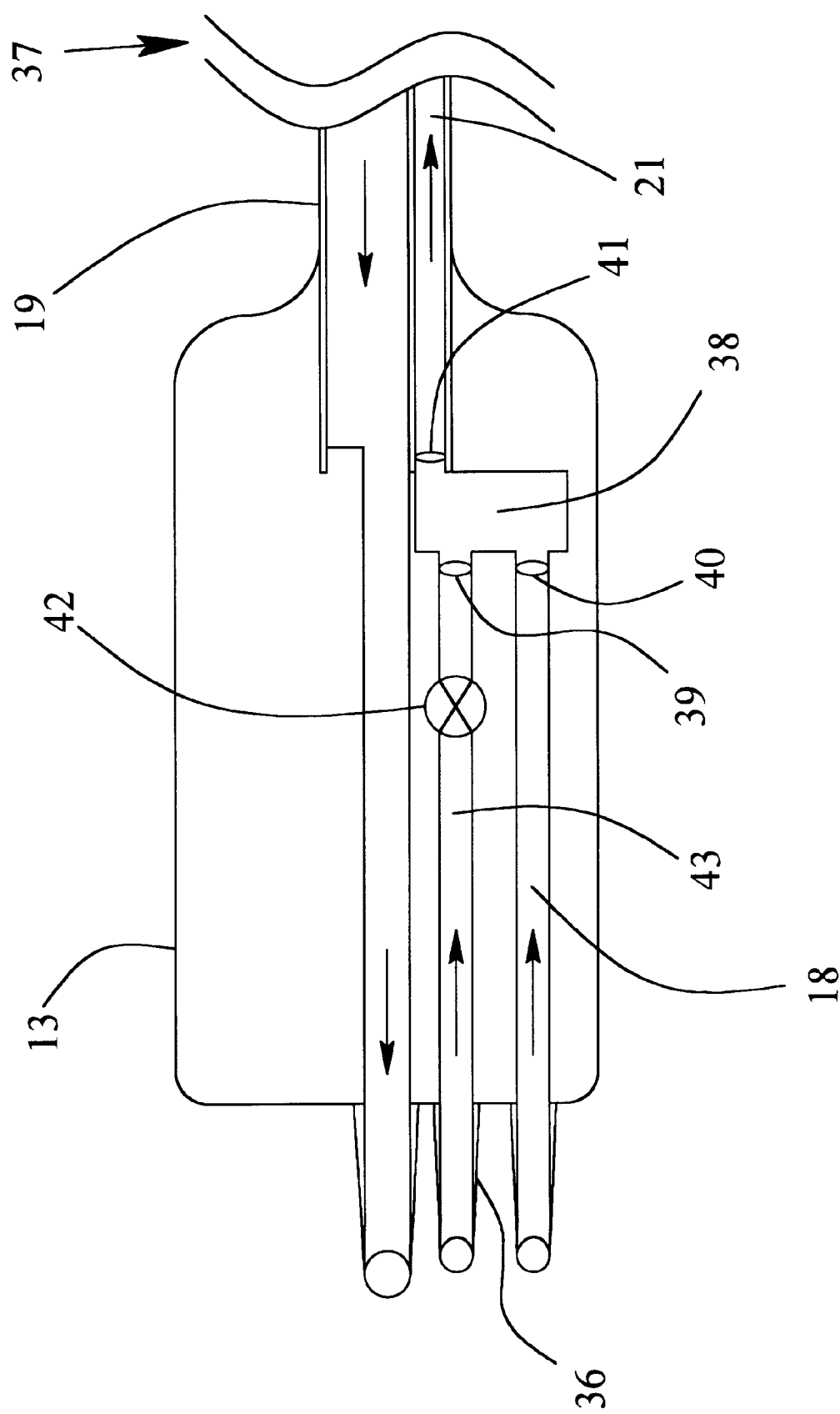
FIG. 8 is a partial schematic representation of the handle showing the gas valve, the gas channel, and the two-input one-output connector.

A final embodiment of the surgical aspirator and irrigator system 10 is shown in FIG. 8. The handle 13 may include a gas connector 36 located on the handle 13 in fluid communication with a supply of filtered, pressurized, biocompatible gas. The handle has a gas channel 43 in fluid communication with the gas connector 36 and a first input 39 of a two-input one-output connector 38. The two-input one-output connector 38 is also commonly referred to as a 'Y fitting'. A second input 40 of the two-input one-output connector 38 is in fluid communication with the irrigation channel 18 passing through the handle 13. The preferred method of creating the gas channel 43 is to use a piece of silicone tubing between the gas connector 36 and the first input 39. An output 41 of the two-input one-output connector 38 is in fluid communication with the second passage 21 in the multi-lumen cannula 19. A gas control valve 42 may be located on the handle 13. The gas control valve 42 selectively opens or closes so that the gas channel 43 passing through the handle 13 is in fluid communication with the first input 39 on the two-input one-output connector 38 when the gas control valve 42 is open or so that the gas channel 43 is sealed from fluid communication with the first input 39 on the two-input one-output connector 38 when the gas control valve 42 is closed. The preferable method of creating the gas control valve 42 is to use a spring and wedge to pinch and occlude the gas channel 43 that has been formed with a piece of silicone tubing. The S-shaped double lines 37 shown in FIG. 8 indicate a break-in-length and are used to scale the diagram to fit on one page. The S-shaped double lines 37 are not part of the invention.

What is claimed is:

1. A surgical aspirator and irrigator system for use by a surgeon for removal of fragmented tissues and fluids from a patient comprising:

a source of suction;

a source of irrigation fluid;

a handle to be held and manipulated by the surgeon, the handle having a distal end;

a suction connector on the handle for fluid communication with the source of suction;

an irrigation connector on the handle for fluid communication with the source of irrigation fluid;

a suction channel passing through the handle in fluid communication with the suction connector;

an irrigation channel passing through the handle in fluid communication with the irrigation connector;

a vent passageway in fluid communication between the ambient air and the suction channel passing through the handle;

a multi-lumen cannula having at least two passages along an axis thereof, the multi-lumen cannula supported on the distal end of the handle;

a first passage within the multi-lumen cannula in fluid communication with the suction channel, the first passage for suction and aligned along the axis;

a second passage within the multi-lumen cannula in fluid communication with the irrigation channel, the second passage for irrigation and aligned along the axis;

a cross-section of the multi-lumen cannula perpendicular to the axis, the cross section located anywhere along the length of the multi-lumen cannula;

a surface area of a unit length of the first passage measured from the cross-section;

a cross-sectional area of the first passage at the cross-section;

a resistive ratio of the first passage that is the surface area of a unit length of the first passage divided by the cross-sectional area of the first passage;

a surface area of a unit length of the second passage measured from the cross-section, a cross-sectional area of the second passage at the cross-section;

a resistive ratio of the second passage that is the surface area of a unit length of the second passage divided by the cross-sectional area of the second passage, the resistive ratio of the first passage between 0.5 and 1.5 times the resistive ratio of the second passage; and the handle includes an irrigation control switch with an electrical connection to an irrigation controller located at and operatively connected to the source of irrigation fluid, the irrigation control switch for initiating or inhibiting the flow of irrigation fluid by electrically signaling the irrigation controller.

2. The surgical aspirator and irrigator system of claim 1 wherein the source of irrigation fluid includes a supply of sterile, biocompatible irrigation fluid.

3. The aspirator and irrigator system of claim 1 wherein the source of irrigation fluid includes a supply of filtered, pressurized, biocompatible gas.

4. The surgical aspirator and irrigator system of claim 1 wherein the system includes:

a supply of sterile, biocompatible irrigation fluid, and a supply of filtered, pressurized, biocompatible gas;

a gas connector located on the handle in fluid communication with the supply of filtered, pressurized, biocompatible gas;

a gas channel passing through the handle in fluid communication with the gas connector;

a two-input one-output connector located within the handle;

a first input on the two-input one-output connector in fluid communication with the gas channel passing through the handle;

a second input on the two-input one-output connector in fluid communication with the irrigation channel passing through the handle;

an output on the two-input one-output connector in fluid communication with the second passage in the multi-lumen cannula;

a gas control valve located on the handle, the gas control valve selectively openable or closeable so that the gas line passing through the handle is in fluid communication with the first input on the two-input one-output connector when the gas control valve is open or so that the gas channel is sealed from fluid communication with the first input on the two-input one-output connector when the gas control valve is closed.

5. The surgical aspirator and irrigator system of claim 1 wherein the resistive ratio of the first passage is between 0.7 and 0.9 times the resistive ratio of the second passage.

6. A surgical aspirator and irrigator system for use by a surgeon for removal of fragmented tissues and fluids from a patient comprising:

a source of suction;

a source of irrigation fluid;

a handle to be held and manipulated by the surgeon, the handle having a distal end;

a suction connector on the handle for fluid communication with the source of suction;

an irrigation connector on the handle for fluid communication with the source of irrigation fluid;

a suction channel passing through the handle in fluid communication with the suction connector;

an irrigation channel passing through the handle in fluid communication with the irrigation connector;

a vent passageway in fluid communication between the ambient air and the suction channel passing through the handle;

a multi-lumen cannula having at least two passages along an axis thereof, the multi-lumen cannula supported on the distal end of the handle;

a first passage within the multi-lumen cannula in fluid communication with the suction channel, the first passage for suction and aligned along the axis;

a second passage within the multi-lumen cannula in fluid communication with the irrigation channel, the second passage for irrigation and aligned along the axis;

a cross-section of the multi-lumen cannula perpendicular to the axis, the cross section located anywhere along the length of the multi-lumen cannula;

a surface area of a unit length of the first passage measured from the cross-section;

a cross-sectional area of the first passage at the cross-section;

a resistive ratio of the first passage that is the surface area of a unit length of the first passage divided by the cross-sectional area of the first passage;

a surface area of a unit length of the second passage measured from the cross-section, a cross-sectional area of the second passage at the cross-section;

a resistive ratio of the second passage that is the surface area of a unit length of the second passage divided by the cross-sectional area of the second passage, the resistive ratio of the first passage between 0.5 and 1.5 times the resistive ratio of the second passage;

a supply of sterile, biocompatible irrigation fluid, and a supply of filtered, pressurized, biocompatible gas;

a gas connector located on the handle in fluid communication with the supply of filtered, pressurized, biocompatible gas;

a gas channel passing through the handle in fluid communication with the gas connector;

a two-input one-output connector located within the handle;

a first input on the two-input one-output connector in fluid communication with the gas channel passing through the handle;

a second input on the two-input one-output connector in fluid communication with the irrigation channel passing through the handle;

an output on the two-input one-output connector in fluid communication with the second passage in the multi-lumen cannula;

a gas control valve located on the handle, the gas control valve selectively openable or closeable so that the gas line passing through the handle is in fluid communication with the first input on the two-input one-output connector when the gas control valve is open or so that the gas channel is sealed from fluid communication with the first input on the two-input one-output connector when the gas control valve is closed.

7. The surgical aspirator and irrigator system of claim 6 wherein the resistive ratio of the first passage is between 0.7 and 0.9 times the resistive ratio of the second passage.

\* \* \* \* \*